United States Patent
Döring

(10) Patent No.: US 9,788,912 B2
(45) Date of Patent: Oct. 17, 2017

(54) FILTER MODULE PACKAGING UNIT

(71) Applicant: B. BRAUN AVITUM AG, Melsungen (DE)

(72) Inventor: Stefan Döring, Dresden (DE)

(73) Assignee: B. BRAUN AVITUM AG, Melsungen (DE)

(*) Notice: Subject to any disclaimer, the term of this patent is extended or adjusted under 35 U.S.C. 154(b) by 0 days.

(21) Appl. No.: 15/416,302

(22) Filed: Jan. 26, 2017

(65) Prior Publication Data

US 2017/0224430 A1 Aug. 10, 2017

(30) Foreign Application Priority Data

Feb. 5, 2016 (DE) .................. 10 2016 102 084

(51) Int. Cl.
| | |
|---|---|
| *B65D 75/00* | (2006.01) |
| *A61B 50/30* | (2016.01) |
| *B65D 85/30* | (2006.01) |
| *B65D 5/42* | (2006.01) |
| *B65D 75/32* | (2006.01) |
| *B65D 81/26* | (2006.01) |
| *B65D 21/02* | (2006.01) |

(52) U.S. Cl.
CPC ............. *A61B 50/30* (2016.02); *B65D 5/42* (2013.01); *B65D 21/0209* (2013.01); *B65D 75/32* (2013.01); *B65D 81/266* (2013.01); *B65D 85/30* (2013.01)

(58) Field of Classification Search
USPC ....... 206/363, 438, 461, 467, 468, 469, 470, 206/471, 205, 210, 207, 213.1
See application file for complete search history.

(56) References Cited

U.S. PATENT DOCUMENTS

| | | | |
|---|---|---|---|
| 6,740,145 B2* | 5/2004 | Boroson | ............... F26B 21/083 |
| | | | 206/204 |
| 2005/0063859 A1 | 3/2005 | Masuda et al. | |
| 2011/0127188 A1* | 6/2011 | Thompson | .............. B32B 27/18 |
| | | | 206/438 |

(Continued)

FOREIGN PATENT DOCUMENTS

| | | |
|---|---|---|
| DE | 10 2007 036 734 | 2/2009 |
| DE | 10 2013 114 010 | 6/2015 |

(Continued)

OTHER PUBLICATIONS

German Search Report for DE 10 2016 102 084.2 dated Nov. 2, 2016 (with translation).

(Continued)

*Primary Examiner* — Jacob K Ackun
(74) *Attorney, Agent, or Firm* — RatnerPrestia

(57) ABSTRACT

A sterile packaging unit of a medical filter module including a filter module packed in a sterile primary package, wherein the primary package is a blister package including a molded part having a receiving compartment for the filter module and a cover part arranged on the molded part and hermetically sealing the receiving compartment, wherein the primary package includes a getter for binding molecular oxygen present in the receiving compartment and the filter module is mounted by form closure with respect to the molded part.

13 Claims, 1 Drawing Sheet

(56) References Cited

U.S. PATENT DOCUMENTS

| | | | |
|---|---|---|---|
| 2012/0067750 A1* | 3/2012 | Bennett | B65D 81/2076 206/213.1 |
| 2012/0091149 A1* | 4/2012 | Pedmo | B65D 21/0219 220/608 |
| 2014/0124397 A1 | 5/2014 | Boggs et al. | |
| 2014/0346081 A1* | 11/2014 | Sowden | A61J 1/035 206/530 |
| 2017/0008686 A1 | 1/2017 | Tanoguchi | |

FOREIGN PATENT DOCUMENTS

| | | |
|---|---|---|
| GB | 2 506 370 | 4/2014 |
| JP | 2006016053 | 6/2006 |
| WO | WO 2015/147 305 | 1/2015 |
| WO | 2015171876 A1 | 11/2015 |

OTHER PUBLICATIONS

Extended European Search Report for European Application No. 17154628.6, dated Jun. 16, 2017, including English translation, 14 pages.

\* cited by examiner

FILTER MODULE PACKAGING UNIT

CROSS REFERENCE TO RELATED APPLICATIONS

This application claims priority to German application DE 10 2016 102 084.2 filed Feb. 5, 2016, the contents of such application being incorporated by reference herein.

FIELD OF THE INVENTION

The invention relates to a sterile filter module/dialyzer packaging unit comprising a filter module/dialyzer (filter cartridge, purifying filter for blood treatment machines etc.) packed in a sterile primary package.

BACKGROUND OF THE INVENTION

When manufacturing sterile medical products, especially filter modules/dialyzers, it has to be ensured that the product remains sterile until use with a patient or use within the scope of treatment. For this purpose, it has to be guaranteed that either the sterile barrier is applied to the product or that the package forms a sterile barrier against the environment which remains intact over the shelf-lifetime stated on the product when realistic storage conditions are assumed.

Filter modules/dialyzers are designed as to their appearance exclusively with respect to requirements in terms of manufacture and application. It is obvious that special requirements to the filter module/dialyzer package are derived from this form. As regards the package, especially standardized, projecting and sharp-edged connectors on the filter module/dialyzer, edges on the filter module/dialyzer and on protection caps of the filter module/dialyzer constitute a problem.

Known packages for medical products, in particular for filter modules/dialyzers, primarily consist of a plastic or aluminum hose or a side-sealed bag (as primary package) as well as of a tray made from plastic material, paperboard or cast fiber and, where necessary, an outer cardboard box (as secondary package). Especially, the tray usually has a shape which substantially corresponds to the shape of the products packed in the primary package so that a kind of form closure is given with a position-stable package is strived for.

Several medical products, especially filter modules/dialyzers, may have to be sterilized in oxygen-free conditions. This means that at the time of sterilization the interior of the primary package has to be completely oxygen-free. As a rule, this is materialized by absorbing the oxygen by an appropriate carrier, a so-called getter. The carrier material may be iron powder or a polymer, for example. The absorber may be supplied to the primary package as a sachet, as it is called, or may be contained in the structure of the packaging material (film).

It is a considerable drawback that the binding of molecular oxygen in the closed-off system of the primary package results in a reduction of volume and, respectively, a vacuum (in non-deformable environment). Known packaging systems are not dimensionally stable, as a consequence the volume thereof is reduced corresponding to the binding of oxygen after closing the package in an uncontrollable manner. Such reduction of volume of the primary packages enables relative movements between packed filter modules/dialyzers inside the secondary package as well as between packed filter modules/dialyzers and the secondary package, wherein said relative movements in turn may result in damage of the sterile barrier.

In known filter module/dialyzer packages the afore-described problems of relative movements due to a reduction of volume during sterilization and ensuing possible damage of the sterile barrier is counteracted by the use of appropriately thick films and/or an oxygen-reduced atmosphere during a packaging process. Both processes have the drawback of entailing high material and processing costs, respectively. It is another drawback that reductions of volume by providing an oxygen-reduced atmosphere in the packaging process cannot be completely excluded, as such package, especially a filter module/dialyzer package must be guaranteed to be 100% oxygen-free. As a result, use of an absorber and reductions of volume resulting therefrom are indispensable. Thicker packaging materials of higher mechanical load capacity for the primary package increase the product costs and still cannot ensure 100% safety to the integrity of the sterile barrier.

SUMMARY OF THE INVENTION

Based on the afore-described state of the art, an object underlying the present invention is to eliminate the afore-listed drawbacks, especially to provide a sterile filter module/dialyzer package with which damage of the sterile barrier due to relative movements between packages enabled by uncontrolled reduction of volume can be minimized or preferably prevented. The package itself preferably is intended to be immune to reduction of volume as well as inexpensive and dimensionally stable.

According to aspects of the invention, this object is achieved by a sterile filter module/dialyzer packaging unit comprising a filter module/dialyzer packaged in a sterile primary package, wherein the primary package is configured as a blister package including a molded part having a receiving compartment for the filter module/dialyzer and a cover member arranged on the molded part and hermetically sealing the receiving compartment, wherein the filter module/dialyzer packaging unit includes a getter for binding oxygen present in the receiving compartment and the filter module/dialyzer is supported by form closure with respect to the molded part.

By the reduction of oxygen in the receiving compartment the filter module/dialyzer stored therein may be finally subjected to radio(gamma) sterilization.

The package of a filter module/dialyzer makes up for a substantial part of its manufacturing costs. By the invention advantageously a reduction of costs can be achieved, as trays used in packages known from the state of the art are no longer required to ensure sufficient dimensional stability of the package despite a reduction of volume by the absorption of oxygen. The hard blister package according to aspects of the invention can be (is) adapted or can be (is) approached especially easily and properly to the shape of the packed filter module/dialyzer. In this way, relative movements between the filter module/dialyzer and the package can be minimized or even eliminated. Automated packaging is possible in a reliable and reproducible manner by exact definition of shape of the hard blister, especially of the molded part thereof.

In accordance with aspects of the invention, a package including hard blister is used for filter modules/dialyzers (or other medical products). It is configured so that, despite a reduction of volume or vacuum formed in the receiving compartment due to oxygen being bound by the getter, no relative movements are allowed between individually packed filter modules/dialyzers. According to one embodiment, this is possible by defining an area inside the package in which the package, especially the molded part, may deform due to a reduction of volume without impairing the overall stability and the basic shape of the package (target position of deformation/target area of deformation). Without impairing the basic shape of the package in this context means that particular outer areas of the primary package which are provided and adapted for the primary package to rest, via said particular outer areas, on other primary packages, for example, or on an outer package (secondary package) will not deform. Preferably, inner portions of the primary package, especially of the molded part, via which or on which the filter module/dialyzer is held, mounted or supported will (thus) remain equally substantially non-deformed. That means that those particular outer areas of the molded part of the primary package which are adapted not (negligibly) to deform, preferably on the inner side constitute also those portions which support the inserted filter module/dialyzer.

Advantageous embodiments of the invention are claimed in the subclaims and shall be detailed hereinafter.

One embodiment of the invention is wherein the molded part is substantially dimensionally stable (i.e. is negligibly deformed during normal operation/in predetermined use). It may include a pressure compensation portion acting as a volume compensation element and is formed to be weakened with respect to the residual molded part. In this sense, the term weakened means that it is designed to have less dimensional stability than other areas of the molded part or the (primary) package. In this way, the molded part can deform, due to vacuum caused in the receiving compartment by the getter binding oxygen, in the pressure compensation portion only. Otherwise it can remain dimensionally stable. It is also true that the primary package includes a volume compensation element which is determined to compensate changes in volume occurring after hermetically sealing the primary package, especially changes in volume caused by the binding of oxygen by the getter (in the target deformation areas). Central points of this embodiment inter alia are the aspects of the regional weakening to obtain controlled and defined reduction of volume, when oxygen present in the receiving compartment is bound, without weakening and especially uncontrolled change of shape of the overall package preferably in the areas by which the primary packages are mutually supported and, further preferred, in the areas by which the inserted filter module/dialyzer is supported.

In another embodiment, the pressure compensation portion may be a configuration bulging outwardly in the unloaded state, especially a lens-shaped configuration. The configuration may be formed into an inwardly bulging configuration due to vacuum prevailing in the receiving compartment as oxygen is bound by the getter. In the unloaded state in this context means that no vacuum is prevailing in the package.

One embodiment of the invention is wherein the filter module/dialyzer includes a substantially cylindrical central portion by which it is supported on a bearing portion of the molded part and is positively retained. The molded part may form, on both sides of the bearing portion, a port receiving structure expanded with respect to the outer contour of the filter module/dialyzer. In said port receiving structure filter module/dialyzer ports formed on each end side of the central portion of the filter module/dialyzer may be accommodated. Preferably, the filter module/dialyzer ports are open in the respective port receiving structure, i.e. are not blocked by the package, especially by the molded part or the cover part. Accordingly, they are freely accessible and are not covered by the primary package so that fluid communication of the interior of the filter module/dialyzer with the receiving compartment, especially with the port receiving volume, is formed. Oxygen present inside the filter module/dialyzer may exit via said fluid communication and may be bound by the getter. In this way, removal of oxygen from the filter module/dialyzer for the purpose of radio(gamma) sterilization is easily and efficiently possible.

One embodiment is wherein the bearing portion is configured to be at least partially semi-cylindrical. In such bearing portion, a cylindrical central portion of the filter module/dialyzer can be accommodated to be guided and mounted in both the radial and the axial directions. The dimensions of the filter module/dialyzer and the bearing portion can be tailored to each other so that the filter module/dialyzer is retained to be slightly clamped in the bearing portion. Due to the semi-cylindrical geometry of the bearing portion, a user still can easily remove the filter module/dialyzer from the package. Clamping may also be achieved, however, by the protection caps, the various connectors as well as any other contour provided on the filter module/dialyzer.

Moreover, a filter module/dialyzer packaging unit according to aspects of the invention may include a secondary package in which a number, preferably a plurality of primary packages each having at least one filter module/dialyzer received therein are arranged so that the primary packages are positively engaged with each other. Especially appropriate form closure between the primary packages can be obtained by the latter, especially the molded part, exhibiting a substantially P-shaped or double P-shaped design especially in the area of the port receiving volume, in cross-section transversely to the longitudinal direction of the filter module/dialyzer. Preferably, the package is designed so that the filter module/dialyzer is accommodated in the head of the P and a filter module/dialyzer port is accommodated in the foot of the P. In this shape as well as in other shapes of the primary package the cross-section of the primary package is designed transversely to the longitudinal direction of the filter module/dialyzer so that two primary packages are in stable engagement when disposed inversely on top of each other. The central point of this preferred embodiment is a tooth system or mutual support of plural primary packages contained in a secondary package for restricting relative movements between said primary packages.

Of preference, contact portions, especially contact faces, are formed in the molded part. They are established and suited to bring about position-stable arrangement on an adjacent primary package. The volume compensation element is preferably disposed outside said contact portions so that the contact portions will not deform when the volume element deforms for volume compensation. It is of particular advantage to a position-stable arrangement when, according to one embodiment, a plurality of primary packages is arranged to be offset relative to each other in the longitudinal direction by half of their longitudinal length so that a respective port receiving structure of two primary packages engage in the clearance formed between the two end-side port receiving structures of a third primary package and fix the three primary packages relative to each other in the longitudinal direction.

Summing up, it is stated that the basic idea underlying the invention is to make use of a hard blister for a sterile package of a filter module/dialyzer. The design of the hard blister according to aspects of the invention preferably is such that the exterior form of the filter module/dialyzer is depicted in the primary package, but gas exchange (oxygen exchange)

between the product and the absorber is possible without obstruction. A (primary) package according to aspects of the invention thus may comprise two central points:

first, a defined weakened zone compensating the reduction of volume inevitably occurring (due to the presence of the absorber) and thus ensures dimensional stability of the (primary) package at least in the crucial areas and second, an exterior stable form which allows for engagement of plural individual/primary packages so that relative movements between grouped individual/primary packages are eliminated.

A reduction of volume is limited to a locally defined area. The overall stability of the primary package substantially is not (negligibly) limited. In one embodiment of the invention a stable stacking capability without any additional intermediate layers in the secondary package is ensured. For this purpose, the outer shape of the hard blister is configured so that plural hard blisters according to aspects of the invention are in mesh and mutually back each other. It can be stated that plural individual packages or primary packages in combination are in mesh so that relative movements between individual packages, especially relative movements in the direction of the longitudinal axis of the individual packages, are possible to a limited extent only or are even impossible. For this reason, the invention allows dispensing with intermediate layers (trays) in the secondary package which have been required so far for packing filter modules/dialyzers.

The invention helps to achieve, inter alia, the following advantages:

saving intermediate layers (trays), improved possibility of automation (handling) resulting especially in a reduction of manufacturing costs, possible arrangement of a large number of filter modules/dialyzers in a cardboard box, resulting especially in a reduction of logistics expenditure, new design options by straight "communication surfaces" between individual primary packages as well as a secondary package, and limitation of various relative movements usually resulting in harms to the package and, consequently, to the sterile barriers.

BRIEF DESCRIPTION OF THE DRAWING

The invention is best understood from the following detailed description when read in connection with the accompanying drawing. Included in the drawing are the following figures.

DETAILED DESCRIPTION OF PREFERRED EMBODIMENTS

In the example configuration described hereinafter a dialyzer and the dialyzer primary package thereof are mentioned. It is noted, however, that instead of the dialyzer any other type of filter module may be provided.

Figure 1:
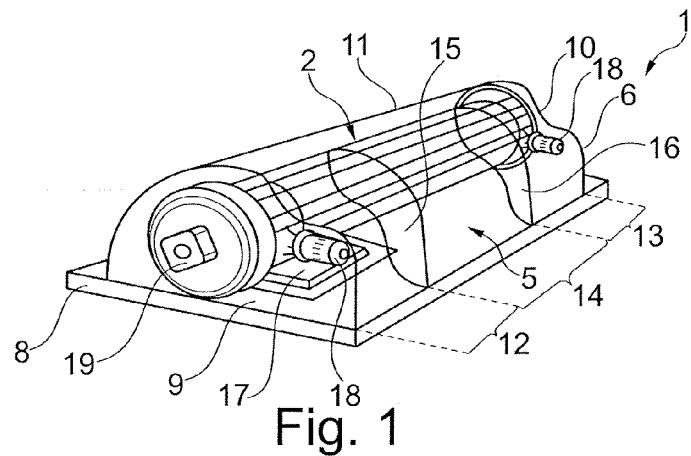
FIG. 1 shows a schematic perspective view of a sterile filter module/dialyzer packaging unit and, respectively, a dialyzer primary package in a first embodiment.
Figure 2:
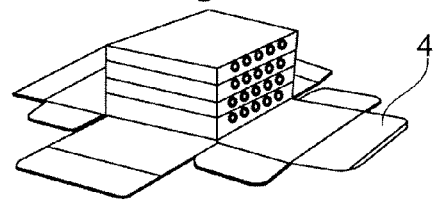
FIG. 2 shows a plurality of sterile dialyzer primary packages of FIG. 1 stacked for being additionally packed in a secondary package.
Figure 4:
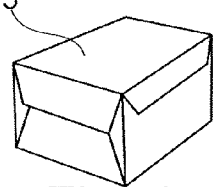
FIG. 4 shows the dialyzer primary package of FIG. 2 in a closed outer package.

The sterile dialyzer primary package 1 (hereinafter also referred to as primary package 1) according to aspects of the invention is illustrated in FIG. 1 with a dialyzer 2 packed to be sterile therein. The dialyzer primary package 1 is combined, along with further dialyzer primary packages 1 including dialyzers packed therein, into a packaging unit with a secondary package or outer package 3. The secondary package 3 is, for example, a folding cardboard box 3 made of a blank 4, as shown in FIGS. 2 and 4.

According to aspects of the invention, the primary package 1 is a hard-hard-blister package comprising a molded part 6 or bottom part 6 forming a receiving compartment 5 for the dialyzer 2. The receiving compartment 5 is hermetically sealed, after arranging the dialyzer 2 therein as defined, by a cover part 7 disposed on the molded part 6. The cover part 7 is a plastic film which is disposed on a peripheral edge 8 of the molded part 6 and is hermetically glued to the same.

The molded part 6 is made from plastic material, for example by molding, and has a defined shape including two stable side walls 9, 10 and a trough 11 disposed there between. The side walls 9, 10 and the trough 11 form the receiving compartment 5 for the dialyzer 2 and on the open side thereof are connected to the peripheral edge 8. Each of the edge portions 12, 13 of the trough 11 adjacent to the respective side wall 9 and 10, respectively, equally exhibits appropriate stability. The term "stable" in this context means that the side walls 9, 10 and the trough portions 12, 13 will not substantially deform when vacuum is formed in the receiving compartment 5 due to binding of oxygen. A central trough portion 14 having reduced dimensional stability as compared to the lateral trough portions 12, 13 is formed between the two lateral trough portions 12, 13. Reduced dimensional stability in this context means that this trough portion 14 will deform at least partially from a first state into a second state when vacuum forms in the receiving compartment 5 due to binding of oxygen and will cause pressure compensation. The areas of the molded part 6 formed of the side walls 9, 10 and the lateral trough portions 12, 13 remain substantially free from deformation.

In the embodiment of the molded part 6 shown in FIG. 1 the central trough portion 14 is connected to the respective lateral trough portion 12, 13 via side wall portions 15, 16. Preferably, said side wall portions 15, 16 are stable and the afore-mentioned deformation of the trough portion 14 is performed substantially there between. The side wall portions 15, 16 form, along with the lateral trough portions 12, 13, contact structures or contact shapes by which other molded parts 6 may be supported with their central trough portion 14 to be stable in position when they are packed in the outer package 3. Accordingly, the central trough portion 14 of a first primary package 1 engages in the clearance formed between the corresponding side wall portion 15 of a second primary package 1 and the corresponding side wall portion 16 of a third primary package 1. As the central trough portion 11 of the first primary package 1 contacts the lateral trough portions 12, 13 of the second and, respectively, third primary packages 1, the latter are mounted and supported in the radial direction. By mutual contact of the side wall portions 15, 16 of the primary packages 1 the latter are mounted and supported in the axial direction.

For binding molecular oxygen present in the atmosphere of the receiving compartment 5 after closing the primary package 1 and removing the same from the atmosphere for sterilization of the packed dialyzer a getter 17 is placed in the receiving compartment 5.

The inner contour of the receiving compartment 5 is configured so that the dialyzer 2 is mounted by form closure with respect to the molded part 6. The stable lateral areas of the receiving compartment 5 formed by the side wall 9 and the lateral trough portion 12 and, respectively, by the side wall 10 and the lateral trough portion 13 form a volume that is larger than the volume of the portions of the dialyzer 2 received therein so that the radial dialyzer ports 18 and axial dialyzer ports 19 thereof are not closed by the molded part 6 or the cover part 7. In this way, the interior of the dialyzer 2 is in fluid communication with the atmosphere of the receiving compartment 5 so that molecular oxygen present also inside the dialyzer 2 may be bound with the getter 17.

Figure 3:
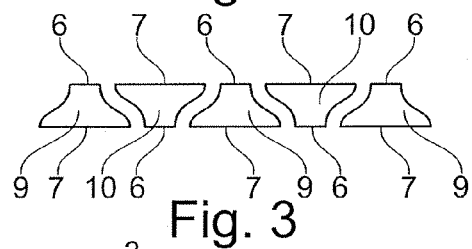
FIG. 3 shows a lateral view of a second embodiment of a sterile dialyzer primary package.
Figure 5:
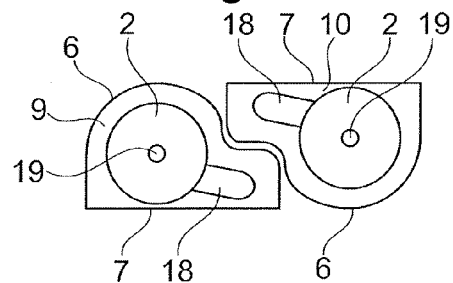
FIG. 5 shows a lateral view of two dialyzer primary packages according to FIG. 1 stacked for being additionally packed.

FIGS. 3 and 5 illustrate in which way a plurality of primary packages 1 is arranged in sort of a 69-arrangement relative to each other to be stable in position for being packed in the outer package 3. In FIG. 5 the P-shaped side contour of the primary packages 1 is clearly visible, with the dialyzer body being received in the head of the P and the dialyzer ports 18, 19 being received in the foot of the P.

The invention claimed is:

1. A sterile packaging unit for receiving a filter module, the sterile packaging unit comprising:
    a blister package comprising a molded part including a receiving compartment configured to receive the filter module and a cover part arranged on the molded part to hermetically seal the receiving compartment, the molded part configured to be dimensionally stable and further including a pressure compensation portion and a residual portion; and
    at least one getter positioned within the receiving compartment for binding molecular oxygen present in the receiving compartment and the filter module;
    wherein the pressure compensation portion of the molded part is configured to deform before the residual portion so that the molded part will deform only in the pressure compensation portion due to vacuum caused in the receiving compartment by the at least one getter binding oxygen.

2. The sterile packaging unit of claim 1, wherein the filter module is a dialyzer.

3. The sterile packaging unit of claim 1, wherein the pressure compensation portion is configured to bulge outwardly prior to the getter binding with oxygen in the receiving compartment and the filter module and to bulge inwardly due to the vacuum caused in the receiving compartment by the at least one getter binding oxygen.

4. The sterile packaging unit of claim 3, wherein the pressure compensation portion is configured to bulge outwardly in a lens-shaped configuration.

5. The sterile packaging unit of claim 1, wherein the molded part further includes a bearing portion and the filter module includes a substantially cylindrical central portion that rests and is positively retained on the bearing portion of the molded part.

6. The sterile packaging unit of claim 5, wherein the molded part on both sides of the bearing portion forms a port receiving structure expanded to accommodate an outer contour of the filter module, the port receiving structure configured to receive dialyzer ports present on each end side of the substantially cylindrical central portion of the filter module.

7. The sterile packaging unit of claim 6, wherein the dialyzer ports are open in the respective port receiving structures and are in fluid communication with the receiving compartment.

8. The sterile packaging unit of claim 5, wherein at least a portion of the bearing portion has a semi-cylindrical shape.

9. A filter package comprising:
    an outer package; and
    a plurality of the sterile packaging units in accordance with claim 1 positioned within the outer package, wherein respective filter modules of the plurality of the sterile packaging units are arranged within the outer package so that the plurality of the sterile packaging units are in positive mesh.

10. The filter package of claim 9, wherein at least a portion of the molded part of each of the plurality of the sterile packaging units has a substantially P-shaped or double P-shaped in a cross-section transverse to a longitudinal direction of the respective filter module, the respective filter module being received in the head of the P and a filter module port being received in the foot of the P.

11. The filter package of claim 10, wherein the cross-section of each of the plurality of the sterile packaging units is configured transverse to the longitudinal direction of the filter module so that two sterile packaging units form a stable mesh when they are arranged inversely on top of each other.

12. The filter package of claim 9, wherein contact portions of the molded part of each of the plurality of the sterile packaging units are configured to produce a position-stable arrangement with an adjacent one of the plurality of the sterile packaging units and wherein the pressure compensation portion is disposed outside of the contact portions.

13. The sterile packaging unit of claim 9, wherein the plurality of the sterile packaging units are arranged to be offset relative to each other in the longitudinal direction by half of their longitudinal length so that a respective port receiving structure of two of the plurality of the sterile packaging units will engage in a clearance formed between two end-side port receiving structures of a third one of the plurality of the sterile packaging units and will fix the three sterile packaging units relative to each other in the longitudinal direction.

* * * * *